(12) United States Patent
Dulski et al.

(10) Patent No.: US 6,428,983 B1
(45) Date of Patent: Aug. 6, 2002

(54) HISTONE DEACETYLASE AS TARGET FOR ANTIPROTOZOAL AGENTS

(75) Inventors: Paula M. Dulski, Jamesburg; Robert W. Myers, Cresskill, both of NJ (US); Anne M. Gumett, Dobbs Ferry, NY (US); Sandra J. Rattray, Somerset; Dennis M. Schmatz, Cranford, both of NJ (US)

(73) Assignee: Merck & Co., Rahway, NJ (US)

( * ) Notice: Subject to any disclaimer, the term of this patent is extended or adjusted under 35 U.S.C. 154(b) by 0 days.

(21) Appl. No.: 09/296,834

(22) Filed: Apr. 22, 1999

Related U.S. Application Data

(62) Division of application No. 08/716,978, filed on Sep. 20, 1996.
(60) Provisional application No. 60/004,065, filed on Sep. 20, 1995.

(51) Int. Cl.⁷ .......................... C12N 21/06; C12N 9/14; C12Q 1/34; A01N 43/02
(52) U.S. Cl. .................. 435/69.2; 435/195; 435/252.3; 435/18; 514/449; 514/895
(58) Field of Search ....................... 435/18, 195, 252.3, 435/69.2; 514/449, 895

(56) References Cited

U.S. PATENT DOCUMENTS

| | | | |
|---|---|---|---|
| 4,218,478 A | 8/1980 | Omura et al. ............... | 514/619 |
| 5,356,927 A | 10/1994 | Taraschi et al. ............ | 514/449 |

FOREIGN PATENT DOCUMENTS

| | | |
|---|---|---|
| EP | 406725 | 9/1991 |
| JP | 07196686 A | 1/1995 |

OTHER PUBLICATIONS

Kervabon et al. (1979) FEBS Letters 106: 93–96.*
Lechner, et al., Biochem, et Biophysica Acta, vol. 1926, No. 2, pp. 181–188 (1996).
Brosch, et al., The Plant Cell, vol. 7, No. 11, pp. 1941–1950 (1995).
Kervabon, et al., Febs Letters, vol. 106, No. 1, pp. 93–96 (1979).
Bioassays, 17(5): p. 423 (1995).
J. Biol. Chem. 268(30): p. 22429 (1993).
J. Antibiot., 43(12): p. 1524 (1990).
Acta Cryst. C., 47: p. 1469 (1991).
Jap. J. Cancer Res., 83(4): p. 324 (1992).
J. Med. Chem., 30: p. 71(1987).
Experientia, 41: p. 348 (1985).
Biochimie, 71: p. 71 (1989).
Tet. Lett., 35(33): p. 6009 (1994).
Biochem., 22: p. 3507 (1983).
J. Med. Chem., 24: p. 567 (1981).
Amino Acids, 6(3): p. 315 (1994).
Biochem., 22: p. 3502 (1983).
Eur. J. Cancer, 10:801 (1974).
Phytopathology, 57: p. 1169 (1967).
Biochem. Biophys. Res. Comm. 107:785 (1982).
Bioch J., 1994, 303: pp. 723–729.
J. Biol. Chem., 1990, 265:17174.
Patent Abstracts of Japan, vol. 95, No. 8, Koji, et al. JP 07196686A.
M. Yoshida, et al., J. Antibiot. (Tokyo), 43(9):1101–1106 (1990).
M. Yoshida, et al., J. Biological Chem., 265(28):17174–17179 (1990).

* cited by examiner

*Primary Examiner*—Tekchand Saidha
(74) *Attorney, Agent, or Firm*—Shu M. Lee; Mollie M. Yang; David L. Rose

(57) ABSTRACT

Histone deacetylase inhibition provides a target for identifying potential antiprotozoal compounds. Histone deacetylase inhibitors are useful as therapeutic agents against protozoal infections.

3 Claims, 2 Drawing Sheets

14C acetate labeled Plasmodium falciparum histone preparation

Trichostatin 500ng/ml
Apicidin 100ng/ml

HISTONE DEACETYLASE AS TARGET FOR ANTIPROTOZOAL AGENTS

This is a division of application Ser. No. 08/716,978 filed Sep. 20, 1996.

BACKGROUND OF THE INVENTION

Parasitic protozoa are responsible for a wide variety of infections in man and animals. Many of the diseases are life threatening to the host and cause considerable economic loss in animal husbandry. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii,* Cryptosporidium sp. are becoming increasingly significant in the developed countries.

A protozoal infection of great economic importance is coccidiosis, a widespread disease of domesticated animals produced by infections by protozoa of the genus Eimeria. Some of the most significant of Eimeria species are those in poultry namely *E. tenella, E. acervulina, E. necatrix, E. brunetti* and *E. maxima*. The disease is responsible for high levels of morbidity and mortality in poultry and can result in extreme economic losses.

In some protozoal diseases, such as Chagas disease, there is no satisfactory treatment; in others, drug-resistant strains of the protozoa may develop. Accordingly, there exists a continued need to identify new and effective anti-protozoal drugs. However, antiparasitic drug discovery has been, for the most part, a random and laborious process through biological screening of natural products and synthetic compounds against a panel of parasites. This process can be greatly facilitated and made more specific if a target of antiprotozoal drugs can be identified, and incorporated into the screening process.

Histone deacetylase and histone acetyltransferase together control the net level of acetylation of histones. Inhibition of the action of histone deacetylase results in the accumulation of hyperacetylated histones, which in turn is implicated in a variety of cellular responses, including altered gene expression, cell differentiation and cell-cycle arrest. Recently, trichostatin A and trapoxin A have been reported as reversible and irreversible inhibitors, respectively, of mammalian histone deacetylase (see e.g., Yoshida et al, Bioassays, 1995, 17(5):423–430). Trichostatin A has also been reported to inhibit partially purified yeast histone deacetylase (Sanchez del Pino et al, Biochem. J., 1994, 303:723–729). Trichostatin A is an antifungal antibiotic and has been shown to have anti-trichomonal activity as well as cell differentiating activity in murine erythroleukemia cells, and the ability to induce phenotypic reversion in sis-transformed fibroblast cells (see e.g. U.S. Pat. No. 4,218,478; Yoshida et al, Bioassays, 1995, 17(5):423–430 and references cited therein). Trapoxin A, a cyclic tetrapeptide, induces morphological reversion of v-sis-transformed NIH3T3 cells (Yoshida and Sugita, Jap. J. Cancer Res., 1992, 83(4):324–328). The present inventors have found that a number of cyclic tetrapeptides structurally related to trapoxin A are inhibitors of histone deacetylase, and also possess antiprotozoal activity.

SUMMARY OF THE INVENTION

The present invention relates to histone deacetylase as a target for antiprotozoal agents. More particularly, the invention concerns a method for identifying potential antiprotozoal agents by determining whether a test compound is capable of inhibiting the action of histone deacetylase. The invention also concerns a method for treating protozoal infections by administering to a host suffering from protozoal infection a therapeutically effective amount of a compound that inhibits histone deacetylase.

DETAILED DESCRIPTION OF THE INVENTION

Figure 1:
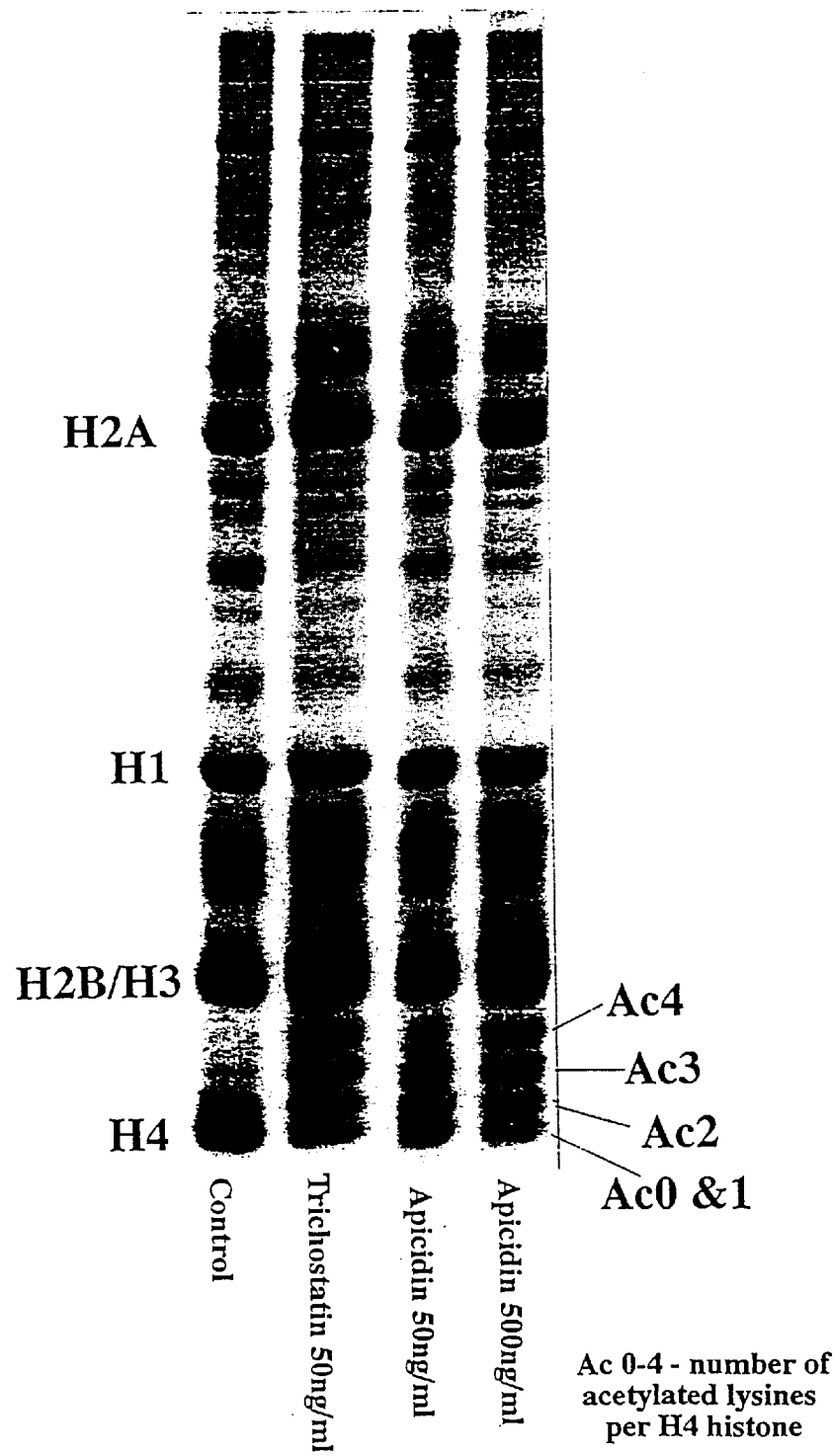
FIG. 1 shows histone deacetylase inhibitors cause hyperacetylation of HeLa cell histones.

In one aspect the present invention provides a method for identifying compounds having antiprotozoal activity comprising:

(a) contacting a histone deacetylase, or an extract containing histone deacetylase with (i) a known amount of a labeled compound that interacts with a histone deacetylase; and (ii) a known dilution of a test compound or a natural product extract; and (b) quantitating the percent inhibition of interaction of said labeled compound induced by said test compound.

In another aspect the present invention provides a method for identifying compounds having antiprotozoal activity comprising:

(a) contacting an intact host or protozoal cell with a test compound or a natural product extract;

(b) disrupting said cell to obtain histones; and (c) determining the level of histone acetylation.

The methods of the invention provides a facile and specific assay to screen compounds as potential antiprotozoal drugs.

In the present invention the histone deacetylase (also referred to herein as HDA or HDAase) may be a purified or partially purified native enzyme, a cloned histone deacetylase or an engineered variant thereof, a crude preparation of the enzyme, or an extract containing histone deacetylase activity. The enzyme may be from a mammalian (e.g. human cervical carcinoma, HeLa cell), avian (e.g. chicken liver or erythrocyte nuclei) or protozoal (e.g. *Eimeria tenella* or *P. berghei*) source; preferably a protozoal histone deacetylase is used. Fragments of histone deacetylase that retain the desired enzyme activity is also within the scope of the invention.

A compound that interacts with histone deacetylase may be one that is a substrate for the enzyme, one that binds the enzyme at its active site, or one that otherwise acts to alter enzyme activity by binding to an alternate site. A substrate may be acetylated histones, or a labeled acetylated peptide fragment derived therefrom such as AcGly-Ala-Lys($\epsilon$-Ac)-Arg-His-Arg-Lys($\epsilon$-Ac)-ValNH$_2$, or other synthetic or naturally occuring substrates. Examples of compounds that bind to histone deacetylase are known inhibitors such as n-butyrate, trichostatin, trapoxin A, as well as other inhibitors described herein. The compound that interacts with histone deacetylase is preferably labeled to allow easy quantitation of the level of interaction between the compound and the enzyme. A prefered radiolabel is tritium.

The test compound may be a synthetic compound, a purified preparation, crude preparation, or an initial extract of a natural product obtained from plant, microorganism or animal sources.

One embodiment of the present method is based on test compound induced inhibition of histone deacetylase activity. The enzyme inhibition assay involves adding histone deacetylase or an extract containing histone deacetylase to mixtures of an enzyme substrate and the test compound, both of which are present in known concentrations. The amount of the enzyme is chosen such that ≤20% of the substrate is consumed during the assay. The assay is carried out with the test compound at a series of different dilution levels. After a period of incubation, the labeled portion of the substrate released by enzymatic action is separated and counted. The assay is generally carried out in parallel with a control (no test compound) and a positive control (containing a known enzyme inhibitor instead of a test compound). The concentration of the test compound at which 50% of the enzyme activity is inhibited ($IC_{50}$) is determined using art recognized method.

Although enzyme inhibition is the most direct measure of the inhibitory activity of the test compound, the present inventors have found that results obtained from competitive binding assay in which the test compound competes with a known inhibitor for binding to the enzyme active site correlate well with the results obtained from enzyme inhibition assay described above. The binding assay represents a more convenient way to assess enzyme inhibition since it allows the use of a crude extract containing histone deacetylase rather than partially purified enzyme. The use of a crude extract may not always be suitable in the enzyme inhibition assay because other enzymes present in the extract may act on the histone deacetylase substrate. The competition binding assay is carried out by adding the histone deacetylase or an extract containing histone deacetylase activity to a mixture of the test compound and a labeled inhibitor, both of which are present in the mixture in known concentrations. After incubation, the enzyme-inhibitor complex is separated from the unbound labeled inhibitors and unlabeled test compound, and counted. The concentration of the test compound required to inhibit 50% of the binding of the labeled inhibitor to the histone deacetylase ($IC_{50}$) is calculated.

In a preferred embodiment, the method of the present invention utilizes a histone deacetylase or an extract containing histone deacetylase obtained from a protozoal source, such as Eimeria or Plasmodium sp.

In a more preferred embodiment, the method of the present invention further comprises determining the $IC_{50}$ of test compounds against host histone deacetylase in either the enzyme inhibition assay or the binding assay as described above, to identify those compounds that have selectivity for parasitic histone deacetylase over that of a host. The assays are the same as previously described, with the histone deacetylase activity obtained from a host of protozoa; for example the host histone deacetylase may be obtained from a mammalian source, e.g. human, or an avian source, e.g. chicken.

Another method useful to identify inhibitors that are selective for parasitic histone deacetylase is the use of acid urea trion (AUT) gel electrophoresis to determine the level of acetylation of histones. Thus compounds that cause hyperacetylation of parasitic histone with no or little hyperacetylation of host histone would be considered selective parasitic histone deacetylase inhibitors.

Where the enzyme inhibition or binding assay utilizes a crude preparation or an extract containing histone deacetylase, the target of the test compound may be verified by examining the level of histone acetylation. Thus, the intact host or parasitic cell containing the enzyme is treated with the test compound. Alternatively, intact host or parasite cells containing the enzyme is treated with test compound in the presence of labeled sodium acetate ($^{14}C$ is the preferred label). In both cases the cells are lysed, histones are partially purified, and analyzed by acid urea triton (AUT) gel electrophoresis. Proteins are detected by staining or by detection of radiolabel by fluorography. Differentially acetylated species can readily be distinguished on such AUT gels due to the slower migration of acetylated species. A histone deacetylase inhibitor will cause hyperacetylation of histones. Since the AUT gel electrophoresis uses intact cells treated with the test compound, this techniques may also be used to identify prodrugs that may be converted to histone deacetylase inhibitor within the cellular environment, but may not be so identified by assay based on the enzyme itself.

In another aspect the present invention provides a method for the treatment of protozoal infections comprising administering to a host suffering from a protozoal infection a therapeutically effective amount of a compound which inhibits histone deacetylase. A therapeutically effective amount may be one that is sufficient to inhibit histone deacetylase of the causative protozoa.

Examples of known compounds which may be histone deacetylase inhibitors and therefore useful in the treatment of protozoal diseases include, but are not limited to, trichostatin A, trapoxin A, HC-toxin, chlamydocin, Cly-2, WF-3161, Tan-1746, apicidin and analogs thereof. Trichostatin A, trapoxin A, HC-toxin, chlamydocin, Cy-2, and WF-3161, as well as derivatives thereof are well known in the art. HC-Toxin is described in Liesch et al. (1982) Tetrahedron 38 45–48; Trapoxin A is described in Itazaki et al. (1990) J. Antibiot. 43, 1524–1532; WF-3161 is described in Umehana et al. (1983) J. Antibiot. 36, 478–483; Cly-2 is described in Hirota et al (1973) Agri. Biol. Chem 37, 955–56; Chlamydocin is described in Closse et al. (1974) Helv. Chim. Acta 57, 533–545 and Tan 1746 is described in Japanese Patent No. 7196686 to Takeda Yakuhin Kogyo KK.

Apicidin and analogs thereof referred to herein have the following structural formulae:

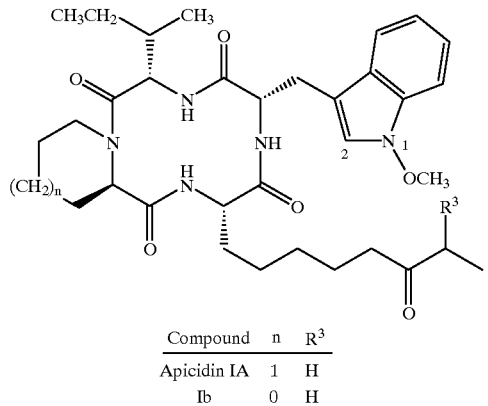

| Compound | n | $R^3$ |
|---|---|---|
| Apicidin IA | 1 | H |
| Ib | 0 | H |
| Ic | 1 | OH |

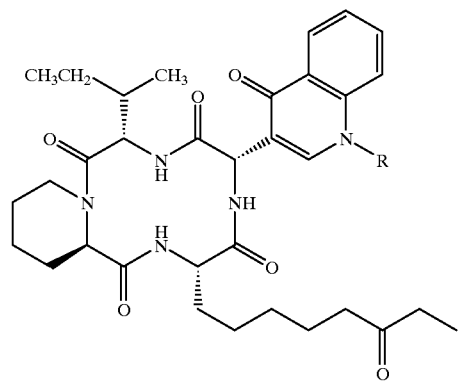

Apicidin IIa  R = OCH3
Apicidin IIb  R = H

Apicidin Ia, Ib, Ic are described in pending applications U.S. Ser. No. 08/281,325 filed Jul. 27, 1994 and 08/447,664 filed May 23, 1995. They are produced from a strain of Fusarium as disclosed in the abovementioned applications.

Histone deacetylase inhibitors are useful as antiprotozoal agents. As such, they may be used in the treatment and prevention of protozoal diseases in human and animals, including poultry. Examples of protozoal diseases against which histone deacetylase inhibitors may be used, and their respective causative pathogens, include: 1) amoebiasis (Dientamoeba sp., *Entamoeba histolytica*); 2) giardiasis (*Giardia lamblia*); 3) malaria (Plasmodium species including *P. vivax, P. falciparum, P. malariae* and *P. ovale*); 4) leishmaniasis (Leishmania species including *L. donovani, L. tropica, L. mexicana,* and *L. braziliensis*); 5) trypanosomiasis and Chagas disease (Trypanosoma species including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) neosporosis (*Neospora caninum*); 8) babesiosis (Babesia sp.); 9) cryptosporidiosis (Cryptosporidium sp.); 10) dysentary (*Balantidium coli*); 11) vaginitis (Trichomonas species including T. vaginitis, and T. foetus); 12) coccidiosis (Eimeria species including *E. tenella, E. necatrix, E. acervulina, E. maxima* and *E. brunetti, E. mitis, E. bovis, E. melagramatis,* and Isospora sp.); 13) enterohepatitis (*Histomonas gallinarum*), and 14) infections caused by Anaplasma sp., Besnoitia sp., Leucocytozoan sp., Microsporidia sp., Sarcocystis sp., Theileria sp., and *Pneumocystis carinii*.

Histone deacetylase inhibitors are preferably used in the treatment or prevention of protozoal infections caused by a member of the sub-phyllum Apicomplexans. More preferably histone deacetylase inhibitors are preferably used in the treatment or prevention of malaria, toxoplasmosis, cryptosporidiosis and trypanosomiasis in humans and animals; and in the management of coccidiosis, particularly in poultry, either to treat coccidial infection or to prevent the occurrence of such infection.

In the case that a histone deacetylase inhibitor is expected to be administered on a chronic basis, such as in the prevention of coccidiosis in poultry, the histone deacetylase inhibitor preferably is selective for protozoal over the host histone deacetylase. Long term administration of such a selective inhibitor would minimize adverse effects to the host due to histone deacetylase inhibition.

Two specific examples of using histone deacetylase inhibitors to prevent the establishment of parasitic infections in humans and animals are 1) the prevention of Plasmodium (malaria) infection in humans in endemic areas and 2) the prevention of coccidiosis in poultry by administering the compound continuously in the feed or drinking water. Malaria is the number one cause of death in the world. The disease is transmitted by mosquitoes in endemic areas and can very rapidly progress to a life threatening infection. Therefore, individuals living in or visiting areas where malaria carrying mosquitoes are present routinely take prophylactic drugs to prevent infection. The histone deacetylase inhibitor would be administered orally or parenterally one or more time(s) a day. The dose would range from 0.01 mg/kg to 100 mg/kg. The compound could be administered for the entire period during which the patient or animal is at risk of acquiring a parasitic infection.

Coccidiosis is a disease which can occur in humans and animals and is caused by several genera of coccidia. The most economically important occurrence of coccidiosis is the disease in poultry. Coccidiosis in poultry is caused by protozoan parasites of the genus Eimeria. The disease can spread quite rapidly throughout flocks of birds via contaminated feces. The parasites destroy gut tissue and therefore damage the gut lining impairing nutrient absorption. An outbreak of coccidiosis in a poultry house can cause such dramatic economic losses for poultry producers that it has become standard practice to use anticoccidial agents prophylactically in the feed. A histone deacetylase inhibitor would be administered in the feed or drinking water for, a portion of, or the entire life of the birds. The dose would range between 0.1 ppm to 500 ppm in the feed or water.

For treatment of established parasitic infections in humans or animals, the histone deacetylase inhibitor could be administered orally or parenterally once the infection is suspected or diagnosed. The treatment period would vary according to the specific parasitic disease and the severity of the infection. In general the treatment would be continued until the parasites were eradicated and/or the symptoms of the disease were resolved. Two specific examples are the treatment of a 1) *Cryptosporidium parvum* infection in an animal or human and treatment of acute *Plasmodium falciparum* malaria in humans. *Cryptosporidium parvum* is a protozoan parasite that infects and destroys cells lining the intestinal tract of humans and animals. The infection establishes quite rapidly and has acute effects on the patient. In the case of humans, patients get severe dysentery for a period of 5–7 days. In immune compromised patients *C. parvum* infections can persist and can be life threatening. In animals *C. parvum* infection is the number one cause of death in young dairy calves. A *C. parvum* infection can be easily diagnosed by symptoms and examination of a stool sample. Once the disease is suspected and/or diagnosed treatment with a histone deacetylase inhibitor can be initiated. The dose would vary between 0.01 mg/kg to 500 mg/kg. Treatments would be one or more time(s) a day, orally or parenterally until the infection is eliminated. Routinely this dosing period would be 1–3 weeks.

*P. falciparum* causes acute life threatening malarial infections in humans. The infection if left untreated can quite often result in death of the patient. A malaria infection can be easily diagnosed by symptoms and examination of a blood sample from the patient. Treatment would be initiated following diagnosis. A histone deacetylase inhibitor would be administered one or more time(s) a day, orally or parenterally, until the infection was eliminated. The dose would range between 0.01 mg/kg to 200 mg/kg.

Histone deacetylase inhibitors may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in human and animals, the dosage may range from 0.01 mg/kg to 500 mg/kg. For prophylactic use in human and animals, the dosage may range from 0.011 mg/kg to 100 mg/kg. For use as an anticoccidial agent, particularly in poultry, the compound is preferably administered in the animals' feed or drinking water. The dosage ranges from 0.1 ppm to 500 ppm.

The compositions of the present invention comprises a histone deacetylase inhibitor and an inert carrier. The compositions may be in the form of pharmaceutical compositions for human and veterinary usage, or in the form of feed composition for the control of coccidiosis in poultry. The term "composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions of one or more of the ingredients. The composition of the present invention thus includes a composition when made by admixing a histone deacetylase inhibitor and inert carrier.

The pharmaceutical compositions of the present invention comprise a histone deacetylase inhibitor as an active ingredient, and may also contain a pharmaceutically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, a histone deacetylase inhibitor can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, histone deacetylase inhibitors may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a histone deacetylase inhibitor may be conveniently administered as a component of a feed composition. Suitable poultry feed composition will typically contain from about 1 ppm to about 1000 ppm, preferably from about 0.01% to about 0.1% percent, by weight of a histone deacetylase inhibitor. The optimum levels will naturally vary with the species of Eimeria involved, and can be readily determined by one skilled in the art. Levels of in poultry feed of from about 0.01% to about 0.1% percent by weight of the diet are especially useful in controlling the pathology associated with *E. tenella,* while the preferred concentration for similar control of intestinal-dwelling species is from about 0.01% to about 0.1% percent by weight of the diet. Amounts of about 0.01% to about 0.1% percent by weight are advantageous in reducing the pathogenic effects of both cecal and intestinal coccidiosis.

In the preparation of poultry feed, a histone deacetylase inhibitor may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

Preparation of Materials Used in the Examples

1. Apicidin (Ia)

(a) Seed Culture of Fusarium sp. ATCC 74322

A portion of agar slant containing Fusarium sp. ATCC 74322 was aseptically transferred to a 250·mL unbaffled flask containing 50 mL of the seed medium having the following composition:

| | |
|---|---|
| Yeast extract (Difco) | 4.0 g/L |
| Malt extract (Difco) | 8.0 g/L |
| Glucose | 4.0 g/L |
| Junlon (polyacrylic acid, Kouyok Trading Co., Tokyo) | 1.5 g/L |
| distilled water | q.v. 1 L |
| pH adjusted to 7.0 prior to sterilization. | |

The culture was incubated on a 2-inch throw gyratory shaker, (220 rpm) for 3 days at 25° C., 85% relative humidity (rh), to obtain biomass. Portions of the biomass were transferred into sterile vials containing glycerol and frozen (as frozen vegetative mycelia). These were maintained in a final concentration of 10–15% glycerol at −75° C.

A vial of the above frozen vegetative mycelia was thawed to room temperature and used to inoculate the seed medium (1 mL per 50 mL seed medium), and the culture was incubated for 2–4 days under the conditions described above. Seed medium of the following composition may also be used to prepare the seed culture:

| | |
|---|---|
| Corn steep liquor | 5.0 g/L |
| Tomato paste | 40.0 g/L |
| Oat flour | 10.0 g/L |
| Glucose | 10.0 g/L |
| Trace element mix* | 10 mL/L |
| distilled water | q.v. 1 L |
| pH adjusted to 6.8 prior to sterilization. | |

*composition (g/L) = $FeSO_4 \cdot 7H_2O$ (1.0); $MnSO_4 \cdot 4H_2O$ (1.0); $CuCl_2 \cdot H_2O$ (0.025); $CaCl_2$ (0.1); $H_3BO_3$ (0.056); $(NH_4)_6MoO_2 \cdot 4H_2O$ (0.019); $ZnSO_4 \cdot 7H_2O$ (0.2).

(b) Production Culture of Fusarium sp.

An aliquot of the seed culture (12 mL) was placed into 220 mL of the liquid portion of the production medium having the following composition:

| | |
|---|---|
| Glucose | 150.0 g/L |
| NZ amine Type A (Sheffield Products) | 4.0 g/L |
| Urea | 4.0 g/L |
| $K_2HPO_4$ | 0.5 g/L |
| KCl | 0.25 g/L |
| $MgSO_4 \cdot 7H_2O$ | 0.25 g/L |
| $ZnSO_4 \cdot 7H_2O$ | 0.9 g/L |
| $CaCO_3$ | 16.5 g/L |
| distilled water | q.v. 1 L (pH 7.0) |

This mixture was swirled vigorously to disperse the biomass and then poured into a 2-liter roller culture vessel which contained 675 cubic centimeters of steam-sterilized large-particle vermiculite (the solid portion). The contents of the roller bottle were shaken/mixed to insure homogeneous inoculation and coverage. The roller bottles were incubated horizontally, revolving at approximately 4 rpm on a Wheaton roller apparatus, at 22° C., 75% rh for 24 days, to obtain secondary metabolite production in the fermentation medium.

The culture also produced the desired metabolites in liquid medium (50 mL in 250 mL unbaffled flask) containing the liquid portion of the above production medium. The flasks were incubated at 22° C., 75% rh for 7–14 days.

Fermentation in 23 L tank fermentor was also carried out using the above liquid production medium. Thus, 10 L of the production medium plus 10 mL of Polyglycol 2000 (Dow) was inoculated with 500 mL of the seed culture, and the fermentation carried out at 21° C., with agitation set at 400 rpm, air flow at 5 L/min and pressure at 0.3 bar. The agitation was increased to 500 and then 600 rpm, and air flow to 10 L/min on day 6 of fermentation (day 0 being the day fermentation started). The fermentation broth was harvested after 14 days for product isolation. The same conditions were also used in 23 L tank fermentation using the production medium whose composition is as follows:

| | |
|---|---|
| Glucose | 150.0 g/L |
| Fructose | 15.0 g/L |
| Sucrose | 40.0 g/L |
| NZ amine Type E (Sheffield Products) | 4.0 g/L |
| Urea | 4.0 g/L |
| $K_2HPO_4$ | 0.5 g/L |
| KCl | 0.25 g/L |
| $MgSO_4 \cdot 7H_2O$ | 0.25 g/L |
| $ZnSO_4 \cdot 7H_2O$ | 0.9 g/L |
| $CaCO_3$ | 8.0 g/L |
| distilled water | q.v. 1 L (pH 7.0) |

(c) Isolation and Purification of Apicidin

The fermentation broth (1.6 L) prepared above was extracted with methyl ethyl ketone (MEK). After evaporating the solvent, the residual aqueous suspension was freeze-dried. The resulting solid mass was extensively triturated with methylene chloride and filtered. The solution was first fractionated at high speed on a 100 ml bed of dry E. Merck silicagel 60 using methylene chloride-methanol 97:3 (v/v). This afforded an enriched preparation of Compound Ia after 0.6 column volumes of washing. Final purification could be achieved by column chromatography on EM silica gel using ethyl acetate in methylene chloride as eluent (1:2 v/v). Yield: approx. 5 mg of homogeneous material.

2. Apicidin analogs Ib and Ic (a) Seed Culture of *Fusarium pallidoroseum*

A portion of agar slant containing *Fusarium pallidoroseum* ATCC 74289 was aseptically transferred to a 250·mL unbaffled flask containing 50 mL of seed medium having the following composition:

| | |
|---|---|
| Yeast extract (Difco) | 4.0 g/L |
| Malt extract (Difco) | 8.0 g/L |
| Glucose | 4.0 g/L |
| Junlon (polyacrylic acid, Kouyok Trading Co., Tokyo) | 1.5 g/L |
| distilled water | q.v. 1 L |
| pH adjusted to 7.0 prior to sterilization. | |

The culture was incubated on a 2-inch throw gyratory shaker, (220 rpm) for 2 days at 25° C., 85% relative humidity (rh), to obtain biomass. Portions of the biomass were transferred into sterile vials containing glycerol and frozen (as frozen vegetative mycelia). These were maintained in a final concentration of 10–15% glycerol at −75° C.

A vial of the above frozen vegetative mycelia was thawed to room temperature and used to inoculate the seed medium (1 mL per 50 mL seed medium), and the culture was incubated under the conditions described above.

(b) Production Culture of *Fusarium pallidoroseum*

An aliquot of the seed culture (12 mL, in the above seed medium) was placed into 220 mL of the liquid portion of the production medium having the following composition:

| | |
|---|---|
| Glucose | 150.0 g/L |
| Fructose | 15.0 g/L |
| Sucrose | 40.0 g/L |
| NZ amine Type E (Sheffield Products) | 4.0 g/L |
| Urea | 4.0 g/L |
| $K_2HPO_4$ | 0.5 g/L |
| KCl | 0.25 g/L |
| $MgSO_4 \cdot 7H_2O$ | 0.25 g/L |
| $ZnSO_4 \cdot 7H_2O$ | 0.9 g/L |
| $CaCO_3$ | 8.0 g/L |
| distilled water | q.v. 1 L (pH 7.0) |

This mixture was swirled vigorously to disperse the biomass and then poured into a 2-liter roller culture vessel which contained 675 cubic centimeters of steam-sterilized large-particle vermiculite (the solid portion). The contents of the roller bottle were shaken/mixed to insure homogeneous inoculation and coverage. The roller bottles were incubated horizontally, revolving at approximately 4 rpm on a Wheaton roller apparatus, at 22° C., 75% rh for 19 days, to obtain secondary metabolite production in the fermentation medium.

(c) Isolation and Purification

Fermentation broth (5.6 liters), as prepared above, containing 225 mg of compound Ia, was extracted with methylethyl ketone by stirring for 2 hours and filtering off the spent biomass. After evaporating the solvent under reduced pressure and freeze-drying the resulting aqueous suspension, the semi-solid residue obtained was taken up in 200 ml of methylene chloride and filtered to remove large amounts of insoluble, unrelated materials.

The solution was again evaporated down and the new residue dissolved in methanol. Fractionation proceeded by gel filtration on a 950 cc column of Sephadex® LH-20 in methanol, whereupon compound Ia and several related analogs eluted after 0.55–0.65 column volumes. There followed a flash chromatography step on a 120 cc E. Merck silica gel 60 column eluted with a step gradient of methanol in methylene chloride. The target compounds again eluted together, in fractions corresponding to the 3% methanol washings.

Material from the first silica gel column was put through a new 120 cc E. Merck silica gel 60 column, this time eluting with a methylene chloride-ethyl acetate 3:1 v/v mixture, and gradually increasing the ethyl acetate content to 100%. This process afforded four fractions, in order of elution, Fraction III contained a mixture of compounds including Ib, and was directly processed by HPLC (same conditions as above). Homogenous compound Ib was found after 15.5 minutes into the gradient.

Fraction IV, on the other hand, was judged to be still too complex for successful HPLC. Accordingly, it was first further enriched by gel filtration on Sephadex® LH-20 before final purification of compound Ic by HPLC (9×250 mm Zorbax® R×$C_8$ column, maintained at 50° C., eluted isocratically for 1 hour with 2 ml/minute 30% aqueous acetonitrile, followed by a 2-hour gradient to 60% acetonitrile). Ve=6.9–7.2 column volumes.

3. Apicidin Analogs IIA and IIB

A solution containing 7.2 mg $Cu^{(II)}(OAc)_2$ in 3 mL methylene chloride and 0.15 mL pyridine under an oxygen atmosphere was prepared. To this was added a solution of 50 mg apicidin in 3 mL methylene chloride in one portion. The solution was stirred at RT for 12 hours and then heated for 4 hours to 45° C. The solvents were removed under reduced pressure and the residue dissolved in 6 mL 1:1 methanol/water to which was added 150 mg $NaIO_4$. the solution was stirred at 40° C. for 48 hours. The solution was diluted with brine, extracted with methylene chloride, the organic layer dried ($Na_2SO_4$), filtered and concentrated under reduced pressure. The crude was partially purified by preparative thin layer chromatography (3×1000 μm silica gel plates) using 1:1 acetone/hexanes as eluant. The lower band was re-purified by preparative TLC (1×1000 μm silica gel plate) using 1:1 acetone/hexanes as eluant yielding Compound IIA (3 mg) and Compound IIB (2 mg). Both compounds gave satisfactory proton NMR spectra.

Physical Properties:

Compound IIA:

$R_f$=0.33 by TLC in 1:1 acetone/hexanes $T_r$=6.1 min in 50:50 acetonitrile/water, 2 mL/min, 4.6×30 cm Zorbax®

RX-8 column

MS: 638 (M+1)

Compound IIB:

$R_f$=0.17 by TLC in 1:1 acetone/hexanes $T_r$=5.7 min in 50:50 acetonitrile/water, 2 mL/min, 4.6×30 cm Zorbax®

RX-8 column

MS: 608 (M+1)

3.2-$^3$H-N-desmethoxyapicidin

Apicidin (25 mg, 0.0401 mmol) was dissolved in sieved (3:2) $CH_2Cl_2$/1-butanol (4 mL) and 20% palladium hydroxide on carbon (ca. 2.5 mg) was added. The system was vacuum-purged thrice with hydrogen gas and the reaction mixture stirred vigorously under 1 atm $H_2$ for 2 h at 23° C. (TLC control; $SiO_2$, 1:1 acetone-hexane; apicidin $R_f$ 0.50, N-desmethoxyapicidin $R_f$ 0.38). The reaction mixture was then filtered through a celite plug, washed thoroughly with methylene chloride and the filtrate concentrated in vacuo. The residue was purified by flash column chromatography ($SiO_2$, 1:3:96 $NH_4OH$—MeOH—$CHCl_3$, 3×9 cm) and concentrated in vacuo to provide N-desmethoxyapicidin (22.2 mg, 23.8 mg theoretical, 93%) as a white powder: Analytical RP-HPLC (gradient elution of 40% acetonitrile-water to acetonitrile at 2 mL/min, peak elution at 8.5 min; Zorbax® Rx-C8, 4.6 mm×25 cm); $^1H$ NMR ($CDCl_3$, 500 MHz) satisfactory; ESI-MS (MeCN—$H_2O$-TFA) m/e 594 ($M^+$, $C_{33}H_{47}N_5O_5$ requires 593.77).

N-Desmethoxyapicidin (10 mg, 0.0168 mmol) was dissolved in sieved $CHCl_3$ (170 $\mu$L) and cooled to 0° C. Pyridinium bromide perbromide (8.1 mg, 0.0253 mmol, 1.5 equiv) was added neat at 0° C. and the reaction mixture was stirred for 45 minutes at 0° C. under an atmosphere of nitrogen (TLC control; $SiO_2$, 1:3:96 $NH_4OH$—MeOH—$CHCl_3$; N-desmethoxyapicidin $R_f$ 0.40, 2-bromo-N-desmethoxyapicidin $R_f$ 0.44). At 0° C. the reaction mixture was quenched with saturated aqueous $NaHCO_3$ and extracted with $CH_2Cl_2$. The organic partition was washed with water, dried over $Na_2SO_4$ and concentrated in vacuo. The crude residue was purified by preparative reverse phase HPLC (gradient elution of 40% acetonitrile-water to acetonitrile at 20 mL/min, peak elution at 22 min) and lyophilized to provide 2-bromo-N-desmethoxyapicidin (4.3 mg, 11 mg theoretical, 40%) as a white powder: Analytical RP-HPLC (gradient elution of 40% acetonitrile-water to acetonitrile at 2 mL/min, peak elution at 9 min; Zorbax® Rx-C8, 4.6 mm×25 cm); $^1H$ NMR ($CDCl_3$, 500 MHz) satisfactory; ESI-MS (MeCN—$H_2O$—TFA) m/e 674 ($M^+$, $C_{33}H_{46}N_5O_5Br$ requires 672.67).

2-Bromo-N-desmethoxyapicidin (2 mg, 0.0030 mmol) was dissolved in sieved $CH_2Cl_2$ (1 mL) and 20% palladium hydroxide on carbon (ca. 0.5 mg) was added. The system was vacuum-purged twice with deuterium gas and the reaction mixture stirred vigorously under 1 atm $D_2$ for 2 h at 23° C. (TLC control; $SiO_2$, 1:3:96 $NH_4OH$—MeOH—$CHCl_3$; 2-bromo-N-desmethoxyapicidin $R_f$ 0.40, 2-D-N-desmethoxyapicidin $R_f$ 0.34). The reaction mixture was then filtered through a celite plug, washed thoroughly with methylene chloride and the filtrate concentrated in vacuo to provide 2-$^3H$-N-desmethoxyapicidin (1.4 mg, 1.8 mg theoretical, 80%) as a white powder: Analytical RP-HPLC (gradient elution of 40% acetonitrile-water to acetonitrile at 2 mL/min, peak elution at 9.8 min for 2-D-N-desmethoxyapicidin and 10.7 min for 2-bromo-N-desmethoxyapicidin Zorbax® Rx-C8, 4.6 mm×25 cm); $^1H$ NMR ($CDCl_3$, 500 MHz) satisfactory; ESI-MS (MeCN—$H_2O$-TFA) m/e 595 ($M^+$, $C_{33}H_{46}N_5O_5D$ requires 594.78).

The above step for converting 2-bromo-N-desmethoxyapicidin to 2-D-N-desmethoxyapicidin was repeated using $^3H_2$ to provide the titled tritiated compound.

4. AcGly-Ala-Lys($\epsilon$-$^{14}C$-Ac)-Arg-His-Arg-Lys($\epsilon$-$^{14}C$-Ac)-ValNH$_2$ To a solution of AcGly-Ala-Lys-Arg-His-Arg-Lys-ValNH$_2$ (0.5 mg, 0.32 umol) in N,N-dimethylformamide (DMF, 20 uL) was added anhydrous sodium carbonate (5 mg) followed by a solution of [$^{14}C$]acetyl chloride in dichloromethane (5 uL, 50 uCi, 0.877 umol, specific activity =57 mCi/mmol). The mixture was stirred at 25° C. for 0.5 h at which time methanol (200 uL) was added and the solution filtered through a plug of glass wool to remove sodium carbonate. The filtrate was concentrated under nitrogen at 45° C. to near dryness and the resulting residue redissolved in methanol (500 uL). The crude product was purified by preparative reversed phase HPLC using a VYDAC™ 210HS54 column (9.4×250 mm) and a mobile phase consisting of a gradient of 5% to 20% acetonitrile/ 0.1% aqueous trifluoroacetic acid over 30 min with a flow rate of 3 mL/min. Fractions containing product were combined, concentrated in vacuo to remove acetonitrile, and the pH adjusted to 6.8 using 1N sodium bicarbonate solution to provide labeled title compound (17 uCi in 4 mL of aqueous solution, estimated specific activity=114 mCi/ mmol) which had a radiochemical purity of >99% as determined by HPLC analysis (VYDAC 210HS54 column, 4.6× 250 mm, mobile phase gradient of 5% to 25% acetonitrile/ 0.1% aqueous trifluoroacetic acid over 20 min, 1 mL/min).

5. AcGly-Ala-Lys($\epsilon$-$^3H$-Ac)-Arg-His-Arg-Lys($\epsilon$-$^3H$-Ac)-ValNH$_2$ To a solution of AcGly-Ala-Lys-Arg-His-Arg-Lys-ValNH$_2$ (3.1 mg, 2.0 umol) in 3:2 DMF-water (100 uL) was added sodium [$^3H$]acetate (40 uL of a 0.2 M solution in 2:1 DMF-water, 8 umol, specific activity=2.9 Ci/mmol) followed by 1-hydroxybenzotriazole hydrate (HOBT, 48 uL of a 0.25 M solution in DMF, 12 umol), 1-ethyl-3-(3-dimethylaminopropyl)carbodiimide hydrochloride (EDC, 48 uL of a 0.25 M solution in DMF, 12 umol) and N-methylmorpholine (NMM, 48 uL of a 0.5 M solution in DMF, 24 umol). The mixture was let stand at 25° C. overnight and acetic acid (20 uL) and methanol (180 uL) were added. The product was isolated by HPLC by multiple injections on a VYDAC 218TP510 column (9.4×250 mm) using a mobile phase gradient of 4% to 16% acetonitrile with 0.1% aqueous trifluoroacetic acid over 16 min with a flow rate or 5 mL/min and detection at 210 nm. Fractions containing product were combined and concentrated in vacuo with continuous flushing with ethanol to remove TFA. The labeled title compound (3.7 mCi, estimated specific activity=3 Ci/mmol) was submitted as a solution in ethanol (1.5 mL) with a radiochemical purity of 92.5% as determined by HPLC analysis (Zorbax® Rx-C8 column, 4.5×250 mm, 15/85/0.1 methanol: water: perchloroic acid, 1 mL/min, 220 nm).

The following non-limiting examples are provided to illustrate the invention.

EXAMPLE 1

Competitive Binding Assay
(a) Preparation of the Lysates

Chick Liver. Livers from 3–5 three week old chickens are collected, rinsed in ice cold phosphate buffered saline (pH 7.4), diced into small pieces and rinsed again 3–4 times with ice cold 50 mM N-2-hydroxyethylpiperazine-N'-2-ethanesulfonic acid (HEPES) (pH 7.4) containing 0.1 mM phenylmethanesulfonyl fluoride (PMSF). The tissue is then resuspended in HEPES buffer, homogenized in a polytron homogenizer and centrifuged at 3000×g for 10 min. The supernatant is then subjected to an additional 100,000 g centrifugation for 1 hour. The pellet and the floating layer of lipid are discarded and the supernatant, referred to as the chick liver S100 fraction, is retained for binding assays. After estimating the protein concentration, the supernatant (S100) is aliquoted and frozen at −80 C.

E. tenella oocysts. Approximately 2×10$^9$ E. tenella oocysts are suspended in 5 ml of PBS/0.1 mM PMSF, 4 mls of an equal mixture (vol/vol) of 4.0 and 1.0 mm glass beads is added. The glass bead-oocyst mixture is then shaken for 20 minutes to cause disruption of the oocysts. The efficiency of breakage is checked microscopically. The resulting homogenate is separated from the glass beads and centrifuged at 3000×g for 10 min. The supernatant is then subjected to an additional centrifugation at 100,000 g for 1 hr. The pellet is discarded and the supernatant, referred to as the E. tenella S100 fraction, is retained for binding assays. After estimating the protein concentration, the supernatant (S100) is aliquoted and frozen at −80 C.

P. berghei. 22.5 mls of blood collected from mice infected with P. berghei malaria (with over 50% of the erythrocytes parasitized) is collected and treated with saponin (1:100 volume of 10% saponin in phosphate buffered saline (PBS)), held on ice for 15 min. to release the parasites and centrifuged at 2000×g for 10 min. The pellet is washed twice in PBS, and then frozen and thawed 3 times in a total vol of 2 ml PBS containing 0.1 mM PMSF (PBS/PMSF). PBS/PMSF is then added to bring the volume up to 10 ml and the suspension is centrifuged at 100,000×g for 1.5 hrs.. The pellet is discarded and the supernatant, refered to as the P. bergheiS 100 fraction, is retained for binding assays. After estimating the protein concentration, the supernatant (S100) is aliquoted and frozen at −80 C.

(b) Competitive Binding Assay

Each assay tube contains a final volume of 1 ml with 1.3 ng/ml of $^3$H-N-desmethoxyapicidin, 150–200 µg of the appropriate S100 supernatant and concentrations of potential HDA inhibitors from 0.001–10 µg/ml.

(i) labeled substrate. 2-$^3$H-N-desmethoxyapicidin (18.69 mCi/mg) is diluted 1:100 in ethanol, and 2 µl added per 1 ml of 50 mM HEPES pH 7.4 with 0.05% Triton-X100 (HEPES/Triton®) is added. This provides 1.3 ng 2-$^3$H-N-desmethoxyapicidin /ml of assay (54,000 DPM/ml.)

(ii) potential HDA inhibitors. The stocks of the test compounds are made up to 2 mg/ml dimethylsulfoxide (DMSO). The stock solution is diluted to 1000, 100, 10, 1 and 0.1 µg/ml in ethanol where a full titration is required. Ethanol is used as a negative control, a 100 µg/ml solution of unlabeled N-desmethoxyapicidin is used as a positive control. Six µl of the test compound solution, the positive and negative controls are used for the assay.

(iii) supernatant from (a). The S100 sample is diluted to a concentration of 3.0 mg protein/ml (chick liver) or 4 mg protein/ml (parasite) in the HEPES/Triton® buffer. Fifty µl is used for the assay.

Stock solutions of potential HDA inhibitors (ii) are diluted into 50 mM HEPES/Triton® buffer to achieve a final concentration of test compound in the range of 0.001–10 µM. $^3$H-N-desmethoxyapicidin is added to a final concentration of 1.3 ng/ml. 50 µl of parasite or chick liver S100 solution (150–200 µg) is added to each tube. The assay mixture is incubated for 1 hr at 25° C. and then aspirated through Whatman GF/B filters impregnated with polyethylenimine (filters prepared in advance by soaking in 2 ml of polyethylenimine per 330 mls water at room temp for 1 hour). Assay tubes were rinsed 3 times with 1–2 mls of HEPES/Triton and aspirated through the same filter. The filter is then dried and counted in scintillant.

Compounds Ia, Ib, Ic, IIA, IIB, trichostatin, trichostatic acid, and HC-toxin were evaluated in the binding assay using E. tenella and chicken liver lysates. Trichostatic acid showed IC$_{50}$ values of >1000 nM in both E. tenella and chicken liver lysates. All the other compounds showed IC$_{50}$ values in E. tenella lysate ranging from 4–60 nM, and except for compounds IIA and IIB, they showed IC$_{50}$ values in E. tenella lysate ranging from 2–35 nM. Compounds IIA and IIB are selective for E. tenella over chicken liver lysate (IC$_{50}$ in chicken liver >1000 nM). The antiparasitic activity of compounds Ia, Ib, Ic, trichostatin, trichostatic acid, HC-toxin were evaluated in vitro against E. tenella (1) and P. falciparum. (2) Trichostatic acid, which showed IC$_{50}$ values of >1000 nM in both E. tenella and chicken liver lysates, was not active against either parasite; the other compounds have minimum inhibitory concentrations ranging from 8 to 250 ng/ml against E. tenella, and IC$_{50}$ ranging from 7 to 115 ng/ml against P. falciparum.

(1) Generally following the procedure described in Crane, Schmatz, Stevens, Habbersett and Murray. Eimeria tenella: in vitro development in irradiated bovine kidney cells.(1984) Parasitology 88: 521–530.

(2) Generally following the procedure described in Desjardins et al, "Quantitative Assessment of Antimalarial Activity In Vitro by a Semiautomated Microdilution Technique" Antimicrobial Agents and Chemotherapy 1979, 16:710–718.

EXAMPLE 2

Determination of Histone Acetylation States
Preparation of HeLa Cell Histones

About 2×10$^7$ HeLa cells growing at 37 C were treated with various compounds in the standard tissue culture medium (MEM containing 10% fetal calf serum) for 4 hrs. Cells were then removed from the flask by scraping in PBS in a total volume of about 10 mls. The cells were washed twice in PBS and resuspended in about 3 mls lysis buffer (Lysis buffer; 0.45% Nonidet® P-40, 10 mM tris, 10 mM NaCl, 5 mM MgCl, 0.1 mM EGTA, 0.1 mM PMSF). The suspension was mixed by vortexing for 10 seconds, incubated on ice for 15 minutes and nuclei were pelleted by centrifugation through a 1 ml cushion of 30% sucrose in lysis buffer at 1300×g for 10 minutes. The supernatant was discarded and the nuclei were then resuspended in 1.0 ml water. H$_2$SO$_4$ was added to a final concentration of 0.4M and the nuclear suspension was incubated on ice for 30 min. and then pelleted by centrifugation at 13,000×g for 10 minutes. The pellets were discarded, and ten volumes of ice cold acetone was added to the supernatant proteins and left overnight at −20° C. to precipitate soluble proteins. These proteins (predominantly histones) were pelleted by centrifugation at 10,000×g for 15 minutes at 4° C. and resuspended in AUT sample buffer (Sample buffer: 0.9M acetic acid, 0.02% w/v methyl green) in preparation for gel electrophoresis.

Gel Electrophoresis

Acid urea triton (AUT) polyacrylamide gels were performed according to the methods of Alfageme et al (1974) J. Biol. Chem. 249, 3729, with modifications as described in Lennox and Cohen (Methods in Enzymology, 170, 532–549). For optimal resolution of HeLa cell and Plasmodium falciparum histones the separation gel contained 7.5M urea, 12% acrylamide, 0.38% Triton® X 100, 0.08% bis acrylamide, and 0.87M acetic acid. The loading gels contained 7.5M urea, 0.37% Triton X 100, 6% acrylamide, 0.04% bis acrylamide and 0.87M acetic acid. Gels were run in 1M acetic acid. Gels were pre-electrophoresed at 350V for 1 hour and run at 450V for 3.5 hours. Gels were either stained with Coomassie Brilliant Blue R in 7% acetic acid, 20% methanol and then destained in 7% acetic acid and 20% methanol, or treated with Enlightening (from New England Nuclear), dried and radiolabel detected by fluorography.

As shown in FIG. 1. apicidin, trichostatin and HC-toxin cause a distinct shift in the histone gel profiles relative to untreated cells. The changes were most distinct for H4 histones. Due to the hyperacetylation of the histones in the treated cells there is a distinct increase in the higher bands of H4 and a decrease in the lower bands for H4. This occurs because the higher the acetylation state of the histones the slower they migrate in the gel.

Labeling P. falciparum with $^{14}$C acetate

Approximately $1 \times 10^9$ P. falciparum infected red blood cells (about 60% parasitized) were resuspended in 10 ml of RPMI 1640 containing various concentrations of test compounds and 250 μCi $^{14}$C sodium acetate and incubated at 37° C. for 2 hours. The cells were then washed 3 time with PBS and histones were prepared as described below.

Preparation of P. falciparumHistones

Histones were prepared according to the method of Cary et al (1994) Parasitology Research, 80, 255–258. P. falciparum infected red blood cells were lysed by the addition of 1/100th volume of 10% saponin in PBS, and the released parasites were washed with PBS and pelleted. Parasites were resuspended in 1 ml hypotonic lysis buffer (10 mM tris pH 8.0, 1.5mM MgCl, 2mM PMSF, 0.2mM N-α-p-tosyl-L-lysine chloromethyl ketone (TLCK), 0.25 μg/ml leupeptin and 10 μg/ml pepstatin), incubated on ice for 15 minutes and lysed with 100 strokes in a dounce homogenizer. A nuclei enriched pellet was obtained by centrifugation at 13,000×g for 10 minutes, the pellet was resuspended in water and histones were prepared and run on AUT gels as described for HeLa cells.

Figure 2:
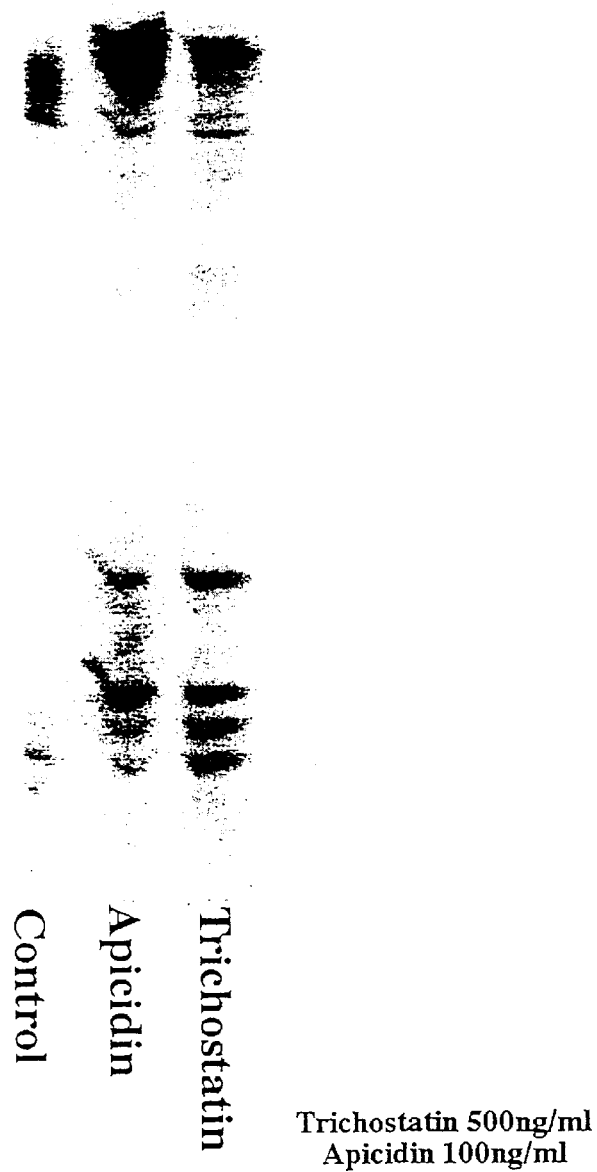
FIG. 2 shows histone deacetylase inhibitors cause hyperacetylation of histones from *P. falciparum*.

As shown in FIG. 2 both apicidin and trichostatin cause hyperacetylation of P. falciparum histones. This is indicated by the overall increase in the amount of 14C-acetylation and a shift in the pattern of the labeled histone bands. The upward shift in treated parasites occurs due to an increase in the population of histones with many acetylated lysines (which migrate slower in the gel) and a decrease in the number of non-acetylated or minimally acetylated (which migrate faster in the gel).

EXAMPLE 3

Histone Deacetylase Inhibition Assay (all temperatures in ° C.)

Assay 1 for Histone Deacetylase Activity and Inhibition

The standard assay contained in a total volume of 40 μL: 400 nmol HEPES-sodium, pH 7.4, 100 pmol of the substrate [AcGly-Ala-Lys($\epsilon$-$^{14}$C-Ac)-Arg-His-Arg-Lys($\epsilon$-$^{14}$C-Ac)-ValNH$_2$] (see Kervabon et al (1979) FEBS Letters 106: 93–96) having a specific activity of approx. 114 mCi/mmol, and a source of histone deacetylase (HDAase) activity. The amount of HDAase added was chosen such that $\leq 20\%$ of the substrate was consumed during the assay. The reaction was initiated by enzyme addition and allowed to proceed for 60 min at 41°. At 60 min, the reaction was terminated by the addition of a 50% slurry of Amberlite® AG 50W×4 cation exchange resin, sodium form (200–400 mesh) in 25 mM sodium acetate buffer, pH 4.2 (200 μL). The resin binds both remaining substrate and the (partially) deacetylated peptidyl products. The quenched reaction was then incubated for at least 30 min at 25° with occasional mixing, diluted with additional 25 mM sodium acetate buffer, pH 4.2 (760 μL; final volume 1000 μL), incubated for a minimum of an additional 30 min at 25° with occasional mixing, and then centrifuged at 10,000×g for 1 min. An aliquot of the supernatant (800 μL) containing the enzymatically released $^{14}$C-acetate was removed, mixed with Aquasol 2 liquid scintillation counter (LSC) cocktail (10 mL), and counted in a Beckman model LS-5801 LSC. To assure that the acetate released was due specifically to the action of HDAase, a parallel control incubation was performed which contained a known HDAase inhibitor [originally, 1–5 mM butyrate (see Cousens et al (1979) J. Biol. Chem. 254: 1716–1723); later, 40–1000 nM apicidin in DMSO once it had been demonstrated to be an HDAase inhibitor]; the amount of radioactivity generated in the presence of inhibitor was subtracted from the value obtained in the absence of inhibitor in order to calculate HDAase dependent acetate production.

For inhibition studies, the inhibitor under examination was added to the standard assay cocktail at the desired concentration in dimethyl sulfoxide (final concentration of DMSO in the reaction was kept constant at 2.5% v/v) and the HDAase activity compared to that found in control (minus inhibitor) incubations which lacked inhibitor but contained 2.5% v/v final DMSO.

Assay 2 for Histone Deacetylase Activity and Inhibition

The standard assay contained in a total volume of 200 μL: 2000 nmol HEPES-sodium, pH 7.4, 11 pmol AcGly-Ala-Lys($\epsilon$-$^3$H-Ac)-Arg-His-Arg-Lys($\epsilon$-$^3$H-Ac)-ValNH$_2$ having a specific activity of approximately 3 Ci/mmol, and a source of histone deacetylase (HDAase) activity. The amount of HDAase added was chosen such that $\leq 20\%$ of the substrate was consumed during the assay. The reaction was initiated by enzyme addition and allowed to proceed for 60 min at 410. At 60 min, the reaction was terminated by the addition of a aqueous solution containing 0.1 M acetic acid and 0.5 M hydrochloric acid (20 μL), followed by the addition of ethyl acetate (1000 μL). The quenched reaction was then vortexed for at least 15 sec at 25° and then centrifuged at 10,000×g for 1 min. An aliquot of the ethyl acetate phase (900 μL) containing the enzymatically released $^3$H-acetate was removed, mixed with Aquasol 2 liquid scintillation counter (LSC) cocktail (6 mL), and counted in a Beckman model LS-5801 LSC. To assure that the acetate released was due specifically to the action of HDAase, a parallel control incubation was performed which contained a known HDAase inhibitor [originally, 1–5 mM butyrate; later, 40–1000 nM apicidin in DMSO once it had been demonstrated to be an HDAase inhibitor]; the amount of radioactivity generated in the presence of inhibitor was subtracted from the value obtained in the absence of inhibitor in order to calculate HDAase dependent acetate production.

For inhibition studies, the inhibitor under examination was added to the standard assay cocktail at the desired concentration in dimethyl sulfoxide (final concentration of DMSO in the reaction was kept constant at 0.5% v/v) and the HDAase activity compared to that found in control (minus inhibitor) incubations which lacked inhibitor but contained 0.5% v/v final DMSO.

Preparation of Hela Nuclear Extract as a Source of HDAase

Hela nuclei were prepared by the method of Cousens et al, supra. The resulting nuclear pellet was hypotonically lyzed by the addition of ~4 volumes of cold 25 mM HEPES-sodium, pH 7.4 and incubation at 4° C. for 10 min with intermittant vortexing. The suspension was then centrifuged at 10,000×g for 10 min at 4° and the resulting supernatant used as a source of HDAase activity.

Preparation of Chicken Red Blood Cell Nuclear Extract as a Source of HDAase

Chickens were sacrificed by asphyxiation with carbon dioxide, decapitated, and bled into a beaker containing one tenth volume of anticoagulant solution (16 mM citric acid, 89 mM trisodium citrate, 16 mM sodium dihydrogen phosphate, 130 mM glucose) on ice. The blood was filtered through four layers of cheesecloth and the erythrocytes sedimented (1500 g, 5 min, 4°) and the supernatant discarded. The erythrocytes were washed twice by suspension in three volumes of buffer A [10 mM Tris chloride, pH 7.2, 50 mM sodium bisulfite, 10 mM magnesium chloride, 0.1 mM phenylmethanesulfonyl fluoride (PMSF), 8.6% w/v sucrose] and subsequent centrifugation (1500 g, 5 min, 4°). The washed erythrocytes were suspended in an equal volume of buffer A, one hundredth volume of 10% v/v saponin added (final concentration, 0.1% v/v), and the suspension incubated for ~20 min with occasion gentle swirling until microscopic examination revealed that >95% of the cells had been lyzed. The suspension was centrifuged (1500 g, 5 min, 4°) to pellet unlyzed cells. The resulting supernatants were carefully poured off, diluted with additional buffer A (two volumes, final of buffer A to starting erythrocytes, 3:1), centrifuged (3000 g, 45 min, 4°), and the supernatants discarded. The resulting nuclear pellets were washed twice by suspension in three volumes of buffer A and subsequent centrifugation (3000 g, 45 min, 4°) followed by a third wash with three volumes of buffer A lacking sodium bisulfite and PMSF. The resulting nuclear pellet was hypotonically lyzed by the addition of ~4 volumes of cold 25 mM HEPES-sodium, pH 7.4 and incubation at 4° for 10 min with intermittant vortexing. The suspension was then centrifuged at 10,000×g for 10 min at 4° and the resulting supernatant used as a source of HDAase activity.

Preparation of Eimeria tenella Extract as a Source of HDAase

Preparation of the S100 extract from *Eimeria tenella* sporulated oocysts was as described above. A portion (2.5 mL) of the extract was concentrated five fold using a centricon ultrafiltration device and the resulting concentrate (500 µL) chromatographed on a Superose 12 HR 10/30 gel filtration column equilibrated with 25 mM HEPES-sodium, pH 7.4. Fractions (500 µL) containing apicidin inhibitable HDAase activity (18–23) were pooled and utilized as the source of Eimeria HDAase activity.

Correlation between HDA Catalytic Activity and Apicidin Binding

When total chick liver homogenate was subjected to ion exchange chromatography an apicidin and butyrate inhibitable HDAse activity coeluted with the 2-$^3$H-N-desmethoxyapicidin binding activity. Partial purification of chicken red blood cell nuclear HDAase by anion exchange chromatography and gel filtration also resulted in coelution of the enzyme activity and the binding activity. Moreover, homogenates of *Eimeria tenella* sporulated oocysts subjected to ammonium sulfate precipitation and gel filtration resulted in the partial purification of a butyrate and apicidin inhibitable Eimeria HDAase which coeluted with 2-$^3$H-N-desmethoxyapicidin binding activity on the column. These data strongly suggested that the binding and enzyme activity were directly related in both host and parasite, and that in fact the target of $^3$H-N-desmethoxyapicidin binding was HDAase. Apicidin, trichostatin, trichostatic acid, HC-toxin and n-butyrate were evaluated in the histone deacetylase inhibition assay (Assay 1), and the results correlate with that obtained in the enzyme and $^3$H-N-desmethoxyapicidin competitive binding assays. Thus, trichostatic acid, which showed no activity in the binding assay, is also inactive in the enzyme inhibition assay. The other compounds showed $IC_{50}$ values in the range of 2–20 nM in the enzyme inhibition assay with *E. tenella* and chicken liver extracts (with the exception of n-butyrate which had $IC_{50}$ values consistent with those reported in the literature). Consequently, a binding assay using an inhibitor or substrate of histone deacetylase as the ligand could be used to identify and design antiprotozoal agents.

What is claimed is:

1. A method for identifying compounds that are antiprotozoal agents by determining whether a test compound or natural product extract inhibits the action of protozoal histone deacetylase, said method comprising:

(a) contacting a protozoal histone deacetylase, or an extract containing protozoal histone deacetylase with a known amount of a labeled compound that interacts with a protozoal histone deacetylase; in the presence or absence of a known dilution of a test compound or a natural product extract; and (b) quantitating the percent inhibition of interaction of said labeled compound by the difference in the enzyme activities in the presence and absence of the inhibitor test compound or natural product extract.

2. The method of claim 1 wherein said labeled compound binds to histone deacetylase.

3. The method of claim 1 wherein said labeled compound is a substrate of histone deacetylase.

* * * * *